US011227077B2

(12) United States Patent
Kadri et al.

(10) Patent No.: US 11,227,077 B2
(45) Date of Patent: Jan. 18, 2022

(54) LABORATORY PHYSICAL PLANT STRUCTURE AND METHOD

(71) Applicant: Kadri Medical Ltd., Windsor (CA)

(72) Inventors: Albert Kadri, Windsor (CA); Mohammed J. Ibrahim, Windsor (CA)

(73) Assignee: Kadri Medical Ltd., Windsor (CA)

( * ) Notice: Subject to any disclaimer, the term of this patent is extended or adjusted under 35 U.S.C. 154(b) by 0 days.

(21) Appl. No.: 16/939,203

(22) Filed: Jul. 27, 2020

(65) Prior Publication Data

US 2020/0356708 A1 Nov. 12, 2020

Related U.S. Application Data

(63) Continuation-in-part of application No. 16/112,835, filed on Aug. 27, 2018, which is a continuation-in-part of application No. 16/751,832, filed on Jan. 24, 2020.

(60) Provisional application No. 62/878,788, filed on Jul. 26, 2019, provisional application No. 62/878,793, filed on Jul. 26, 2019, provisional application No. 63/018,830, filed on May 1, 2020.

(51) Int. Cl.
*G06F 30/13* (2020.01)
*G16H 40/20* (2018.01)

(52) U.S. Cl.
CPC ............. *G06F 30/13* (2020.01); *G16H 40/20* (2018.01)

(58) Field of Classification Search
CPC ................................ G06F 30/13; G16H 40/20
See application file for complete search history.

(56) References Cited

U.S. PATENT DOCUMENTS

| | | | |
|---|---|---|---|
| 2008/0221919 A1* | 9/2008 | Cates | G16H 10/60 705/2 |
| 2013/0128035 A1* | 5/2013 | Johns | G01F 23/20 348/135 |
| 2015/0276775 A1* | 10/2015 | Mellars | G01N 35/0092 436/501 |

* cited by examiner

*Primary Examiner* — Matthew Mikels
(74) *Attorney, Agent, or Firm* — The Dobrusin Law Firm, PC

(57) ABSTRACT

A laboratory physical plant structure and corresponding method disclosed herein improves the time and efficiency of processing of laboratory samples. One embodiment includes a physical arrangement of the bloodletting stations and sorting of specimens including two levels wherein sorting and collection occurs on Level 1 and Processing occurs on Level 2. A lift or other transportation system between the levels is utilized to quickly process and move the samples being collected and tested.

5 Claims, 14 Drawing Sheets

LABORATORY PHYSICAL PLANT STRUCTURE AND METHOD

This application is a continuation-in-part application of U.S. application Ser. No. 16/112,835 filed on Aug. 27, 2018, a continuation-in-part application of U.S. application Ser. No. 16/751,832 filed on Jan. 24, 2020, claims priority and benefit to Provisional Patent Application Ser. No. 62/878,788 filed on Jul. 26, 2019, claims priority and benefit to Provisional Patent Application Ser. No. 62/878,793 filed Jul. 26, 2019, and claims priority and benefit to Provisional Patent Application Ser. No. 63/018,830 filed May 1, 2020.

TECHNICAL FIELD

The present specification generally relates to a system and method of organizing a laboratory and, more specifically, a system and method for laboratory physical plant structure

BACKGROUND

Typically, community-based laboratories are separate operational entities and often in separate locations from medical clinics, typically being in separate building and owned by separate entities. In some scenarios, bloodletting is often done within a clinic but is then shipped to a centralized laboratory for processing. In a community-based setting patients typically visit a laboratory approximately 1-2 weeks prior to a clinic appointment in order to allow time for processing and information to be sent to their practitioners to be reviewed at their clinic appointments. This creates the need for two separate visits for laboratory investigations and then subsequent clinical assessment by practitioners. This aforementioned process is inefficient for the patients and does not allow for immediate same-day results to be used in clinical decision-making. Typically decisions are made based on lab work obtained 1 to 2 weeks prior to the clinic visit. In addition, if the patient forgets to do their lab work, it is often a less impactful clinic visit, with the need to subsequently do the lab work after the clinic visit and follow up on the results without the patient present to be fully informed of their status.

Barriers to having laboratory investigations done on the same visit to the clinical practitioner are multiple. These barriers include the efficiency and processing of bloodletting from patients, remote locations of the central laboratory from clinical practices with bloodletting done and samples being shipped to the central location.

Accordingly, a need exists for an improved laboratory physical layout and process to allow bloodletting to occur within a clinic setting on the same floor to allow for convenience, efficiency and coordination with clinic visits with a separate yet physically connected full laboratory outside of the clinic setting in view of the aforementioned disadvantages.

In the medical field, it is standard to have a primary care physician office fully separate and spaced apart from any specialist physician. As is standard, a patient will first visit a primary care physician and then, if required, be referred to a specialist. The patient must then make an appointment with that specific specialist, often many months later. If desired, the patient must then make a separate appointment with another specialist for a second opinion.

As a background in one application of medicine, vascular healthcare is examined. Cardiovascular disease is a leading cause of death in North America and has become a public health epidemic. Cardiovascular disease and the associated risk factors are linked to an increased risk of morbidity and mortality and are also responsible for escalating healthcare costs. Traditionally, if a primary care physician thinks that a patient should be examined by a cardiologist, the patient is referred to a cardiologist and must make an appointment with the cardiologist's office, often at an entirely different location. When a second opinion is desired, as is often the case, the patient is again responsible for making an appointment. This system delays healthcare delivery to the patient, is time consuming, inconvenient and very costly. Separate EMRs (electronic medical records), and poor information sharing adds to the dysfunctional delivery of care. The current system is highly disjointed and inefficient for practitioners and patients alike.

Typically, a high risk vascular patient must visit several different specialist physicians (cardiologist, endocrinologist, nephrologist, etc.), medical laboratories, imaging facilities, a pharmacy, and their primary care physician. Usually, each of these encounters occurs at different locations and together comprise basic healthcare. The clinical information from each of these separate encounters is not readily available to the individual healthcare providers and is almost always not available to the patient. This process results in the patient being less involved in their healthcare decisions. The patient is further burdened with the responsibility of coordinating multiple appointments (and time away from work) to manage their health.

Accordingly, improved approaches are needed within healthcare systems to address this epidemic and improve patient education, attendance, and adherence to strategies known to improve health outcomes while limiting financial burden. As such, a need exists in an improved medical clinic design, enhanced by an improved clinic layout and multi-specialty care and integrated technologies suited to optimize the patient's time in clinic, healthcare involvement and overall health outcomes.

SUMMARY

The present laboratory physical plant structure and corresponding method disclosed herein improves the time and efficiency of processing of laboratory samples. One embodiment includes a physical arrangement of the bloodletting stations and sorting of specimens including two levels wherein sorting and collection occurs on Level 1 and Processing occurs on Level 2. A lift or other transportation system between the levels is utilized to quickly process and move the samples being collected and tested.

A medical facility comprising a building, the building including a plurality of four segregated specialty areas, each of the specialty areas positioned in the outer four corners of the building, the specialty areas bring a laboratory, an urgent care facility, a pharmacy, and an imaging center, the laboratory having a first level and a second level, the first level configured to collect samples from patients to be tested, the second floor configured to process the samples collected on the first level, a transportation system connecting the first level to the second level, the transportation system configured to transport samples collected on the first level to the second level for immediate processing of the samples on the second level thereby enabling expediting processing of the samples collected on the first level of the laboratory of the medical facility.

In some embodiments, the transportation system is a lift configured to move samples. In some embodiments, the transportation system transports reusable supplies back down to the first level after processing. In some embodiments, a plurality of lifts are provided in the laboratory enabling communication between the first level and the second level. In other embodiments, the transportation system is a elevator configured to hold only samples and supplies.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The present laboratory physical plant structure and corresponding method disclosed herein improves the time and efficiency of processing of laboratory samples. One embodiment includes a physical arrangement of the bloodletting stations and sorting of specimens including two levels wherein sorting and collection occurs on Level 1 (within clinic setting) and Processing occurs on Level 2 (separate from clinic setting). A lift or other transportation system between the levels is utilized to quickly process and move the samples being collected and tested.

The optimal clinical set up is to have the bloodletting procedure, processing and availability of data to clinicians by performing this process within 15 to 20 minutes, immediately prior to the clinic visit, In an efficient manner to allow real time clinical decision-making based on the most current available data.

The present specification discloses a medical clinic layout including a waiting room, reception area, modular clinic pods, patient exam rooms, physician workspace and collaboration area, pharmacy, laboratory, urgent care, imaging . . . etc. along with corresponding flow arrows to illustrate the optimization of the medical clinic layout's efficiency. The present application includes a unique physical and operational design for a vascular health clinic, by way of example. It should be understood that the present clinic layout can apply to various different health specialties and practices and is not limited to vascular health. These components are specifically fashioned to work synergistically to increase the efficiency of healthcare delivery and improve health outcomes, while also moving away from provider-centered care to patient-centered care. The design also minimizes the area required to provide multidisciplinary and multispecialty healthcare.

The design of the present specification is configured to eliminate the fundamental problems, as previously described, with the current healthcare model. Patients will have access to their primary care physician, a select group of vascular health specialists, including cardiology, nephrology, endocrinology, neurology, and vascular surgery (available on-demand for 'quick' problem specific consultation), a medical laboratory, imaging, diagnostics, and pharmacy services, all at the same location, and in the same visit. A corresponding computer application and companion mobile device application are also provided.

By implementing the below described design and utilizing the corresponding computer program and companion mobile device application, healthcare providers will be able to increase the efficiency and quality of healthcare delivery, facilitate and simplify coordination of care, enhance patient involvement in healthcare and measure and improve health outcomes in patients with vascular disease through clinical evidence-based strategies. By implementing this complete design, a new gold standard of healthcare will be achieved.

Figure 1:
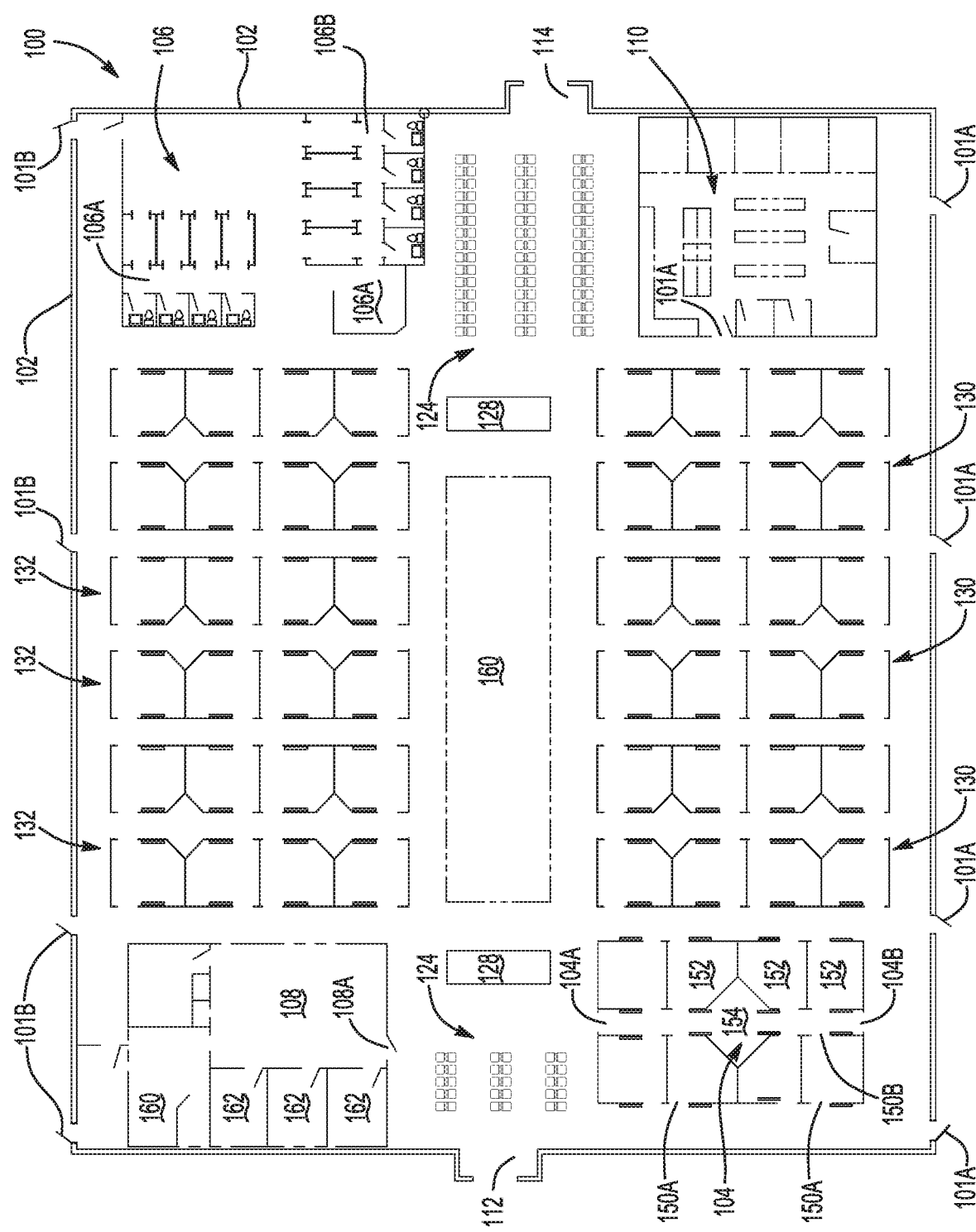
FIG. 1 depicts an exemplary first floor medical clinic layout having waiting rooms, a lab, reception, primary care pods, specialist pods, pharmacy, urgent care, and imaging . . . etc. according to one or more embodiments shown and described herein.

Referring now to FIG. 1, the exemplary clinic layout 100 is generally rectangular or square in shape, having a main outer perimeter 102. The layout 100 includes a four corners design for ancillary components of this unique clinic design, with clinic space centralized between these components. This allows for more efficient coordination of multidisciplinary and multispecialty services and allows these services to be provided in one location, within a smaller footprint. The four corners include an urgent care space 104, a lab 106, an imaging center 108, and a pharmacy 110. The layout further includes two main entrances 112 and 114. The main entrances 112 and 114 include a waiting areas 124 and reception desks 128. Both main entrances 112 and 114 allow patients access to their desired service, either main clinic or ancillary services. This design provides patients with isolated and integrated care and utilizes unidirectional patient flow increase healthcare delivery efficiency. The outer perimeter 102 of the layout 100 further includes exits 101A and 101B, which are configured to be exits only. In the present embodiment, the entrances 112, 114, are configured to be entrances only. The entrances and exits are stationed to be polar opposite sides of the structure, as located at 101A, 101B.

The urgent care space 104 includes an enclosed space set up similar to the primary care and specialty care pods. The urgent care space includes a center hallway 154 where care providers work. Patients are not permitted in the center hallway 154. A plurality of exam rooms 152 are positioned adjacent to the hallway 154. Each of the exam rooms 152 include two doors. One of the doors 150A is a dedicated door for patients. The other door 150B is a dedicated care provider door. Patients are not permitted to pass through the door 150B.

The lab 106 includes a lab reception area 106A where patients check in. The lab is an area where care provides can collect and test samples from patients including urine, blood . . . etc. Areas 106A, 106B includes exam rooms and bathrooms for sample collection spaced apart by a hallway.

The imaging center 108 includes a plurality of rooms for x-ray and ultrasound as shown at 160, 162. The imaging center includes two doors, both near reference numeral 108A to facilitate patient flow through the imaging center.

The pharmacy 110 includes a door 110A located near both a side exit and a main entrance so as to facility patient flow through the pharmacy.

Figure 2:
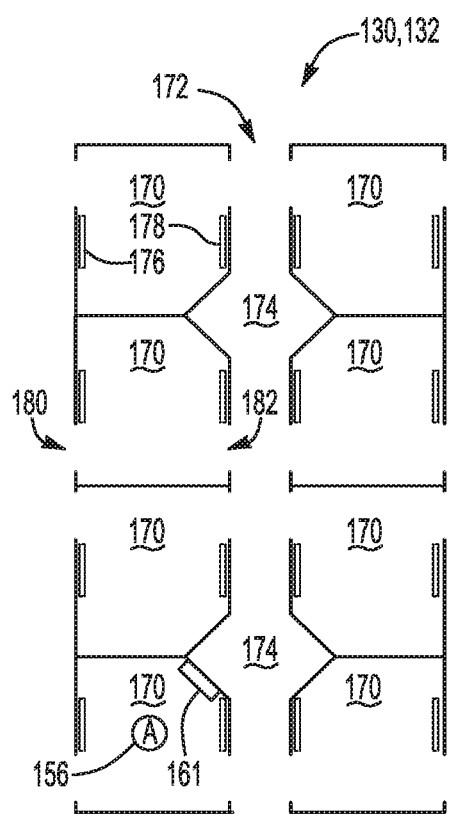
FIG. 2 depicts an exemplary pod (either primary care or specialist) according to one or more embodiments shown and described herein.

The layout 100 further includes a plurality of primary care pods 130 and specialist pods 132. Each of the pods 130,132, as illustrated in FIG. 2, include a plurality of 8 exam rooms 170 each having a patient entrance/exit 180 and a care provider entrances/exit 182. The hallway 172 and the care provider space 174 is only accessible by the care providers, doctors, nurses . . . etc. The hallway 172 and the care provider space 174 shall not be accessible by any patients. The specific layout prevents unwanted interaction between care providers and patients by keeping the spaces that each party walks and moves separate. The patients go in and out of one door (180) and the care providers only go in and out of the other door (182). This specific layout prevents patients from overhearing care providers discussing the files and confidential information of other patients since only care providers are permitted in the hallway 172 and the care provider space 174. Each of the exam rooms 170 may further includes screen 161 and exam table/reclining chair 156.

It should be noted the layout 100 is nearly exemplary and not intended to limit the scope of the present invention. The layout 100 must comprise four corners and a plurality of pods, although the exact configuration, such as shown in FIG. 1, is not required and the specifics of each area may be adjusted in accordance with community needs.

Figure 3:
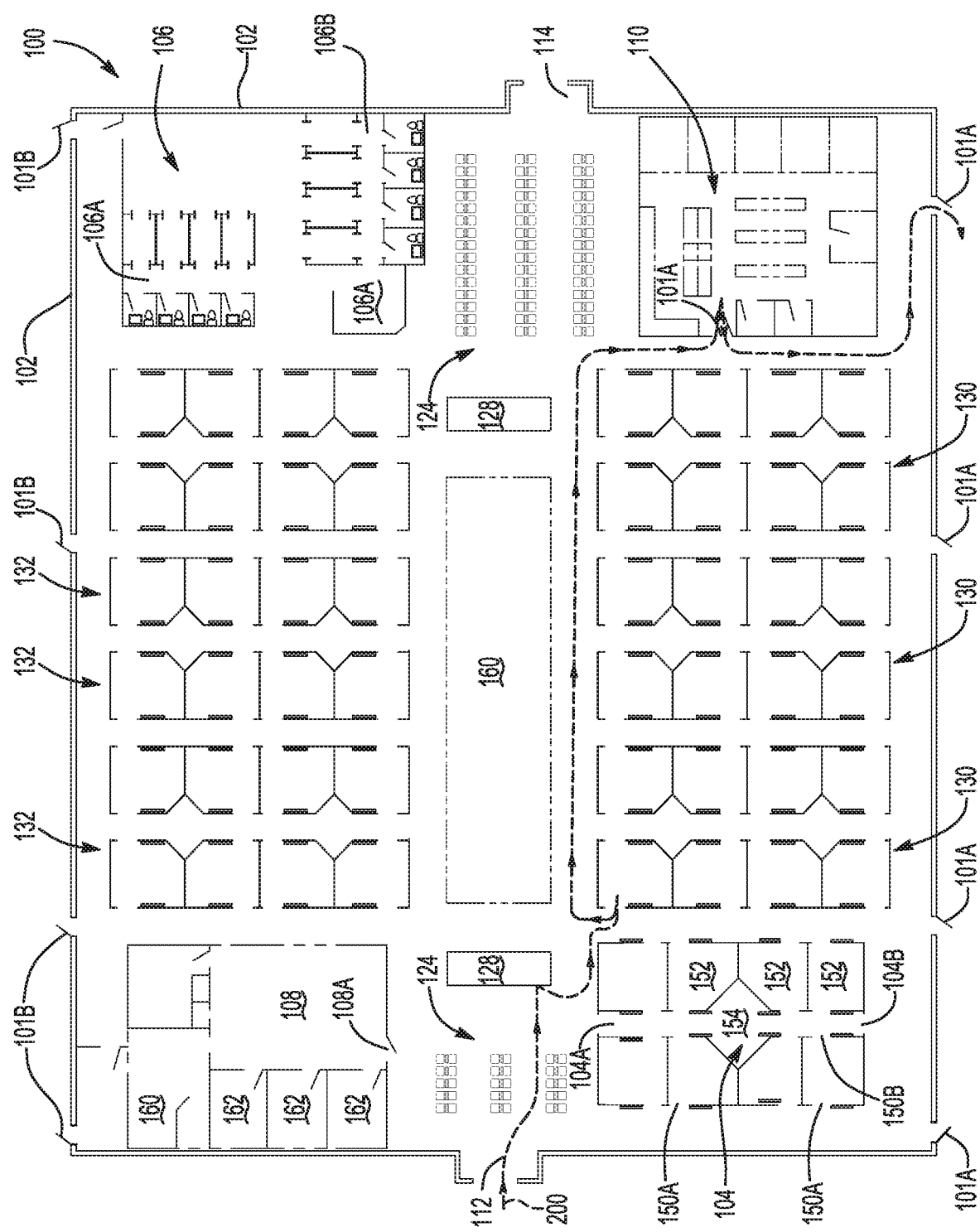
FIG. 3 depicts an exemplary building structure with illustrative flow arrows extending therethrough according to one or more embodiments shown and described herein.

FIGS. 3 through 7 illustrate exemplary paths taken by a patient when visiting the clinic 100. FIG. 3 depicts a patient path 200 wherein the patient enters the main entrance 112 and continues through the waiting area 124. After visiting reception 128 the patient moves to their designated primary care pod 130. The patient may then utilize the pharmacy 110 before exiting 122. Movement of the patient along the patient path 200 facilitates unidirectional patient flow through the clinic. In many embodiments, this flow is clockwise. The patient path 200 facilitates patient movement from the entrance 112 to one of the dedicated exits, in this embodiment, exit 101A, so as to increase clinic operational efficiency. This is further facilitated by the electronic standard adopted by the clinic, ensuring there is no need for patients to backtrack at any time facilitated by a 3D rendering of the path to take through the clinic by the companion phone application.

Figure 4:
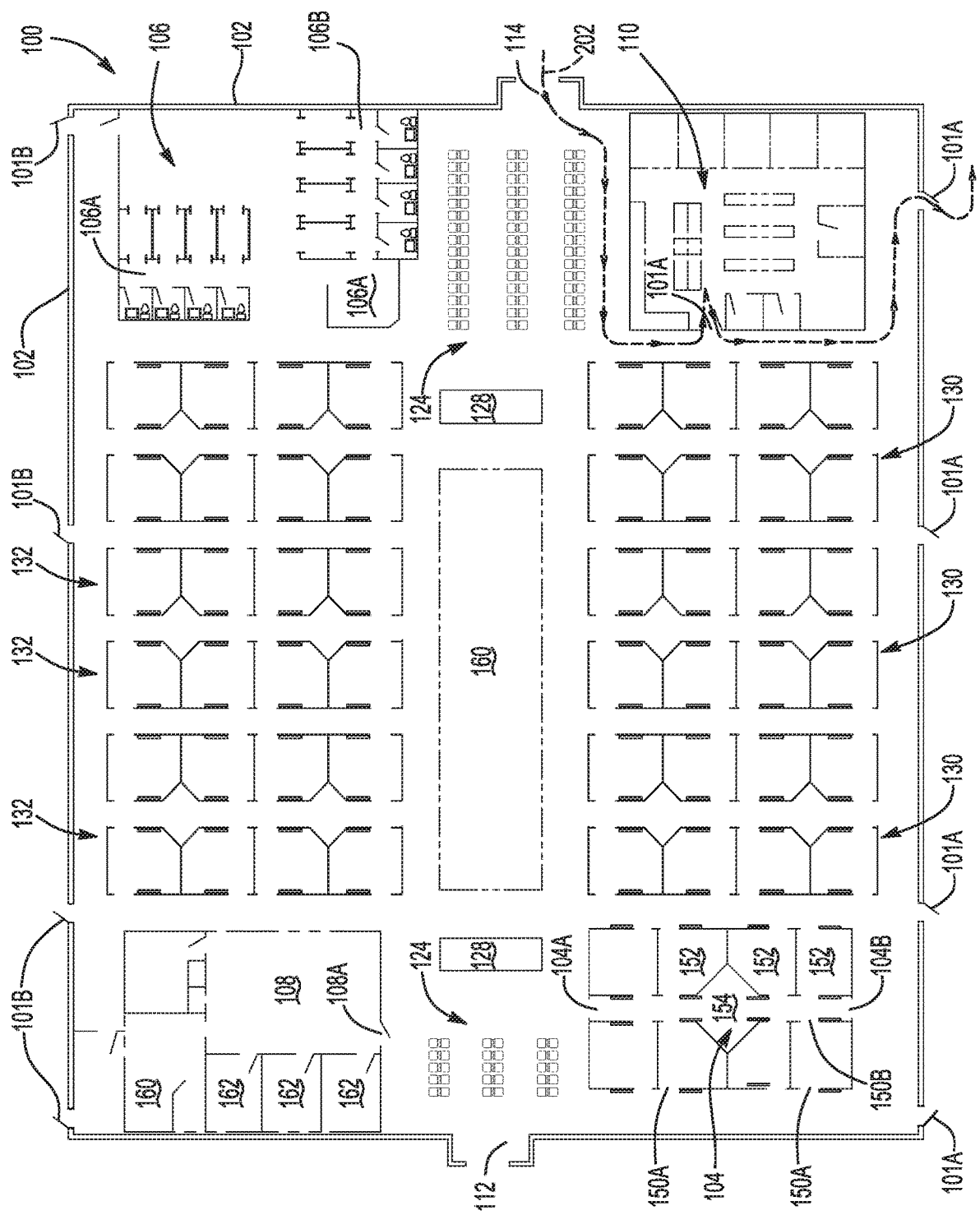
FIG. 4 depicts an exemplary building structure with illustrative flow arrows extending therethrough according to one or more embodiments shown and described herein.

FIG. 4 depicts an exemplary patient path 202 wherein the patient is only visiting the clinic to visit the pharmacy 110. In this embodiment, the patient enters the main entrance 114 and visits the pharmacy 110 before exiting the dedicated exit 101A.

Figure 5:
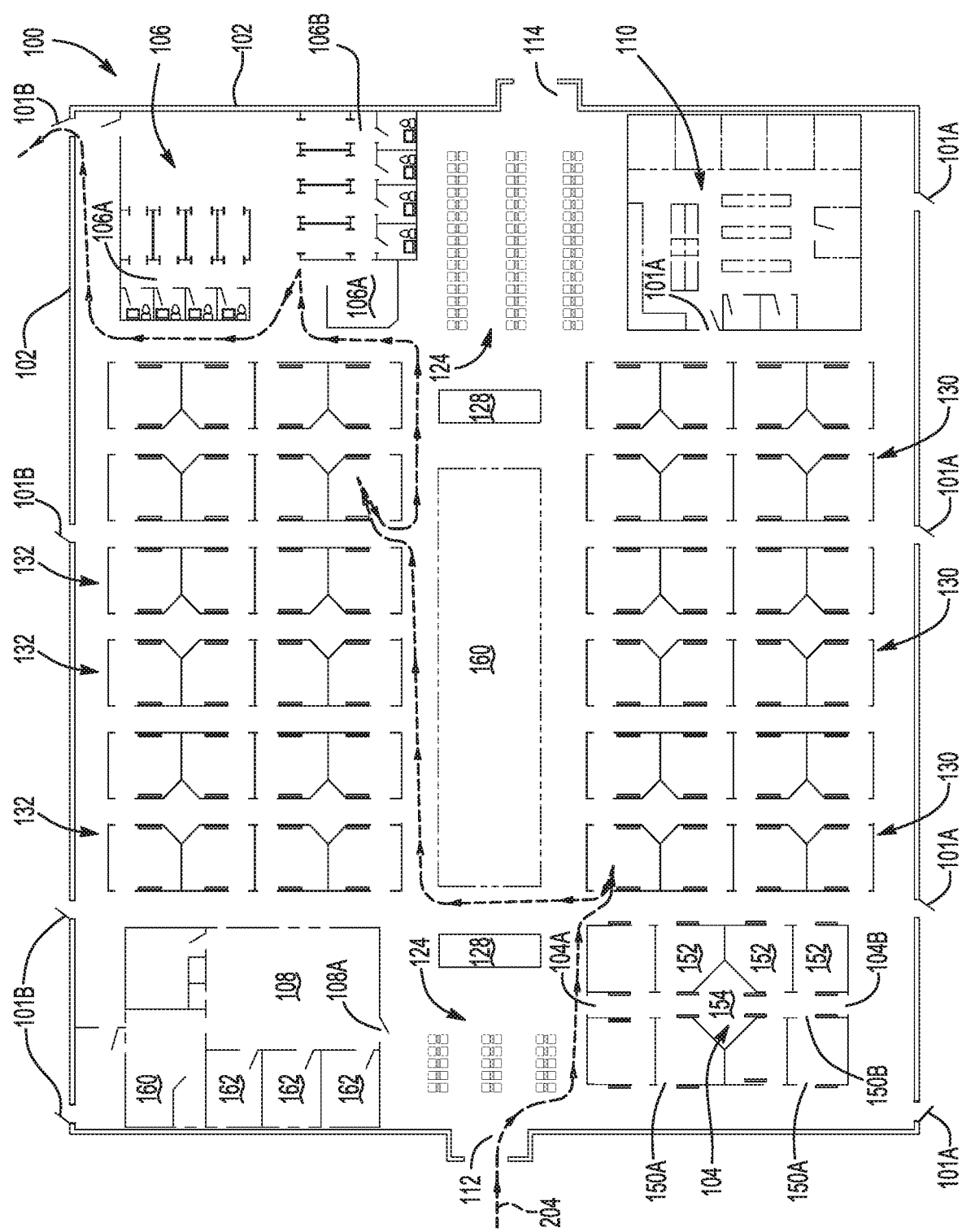
FIG. 5 depicts an exemplary building structure with illustrative flow arrows extending therethrough according to one or more embodiments shown and described herein.

Referring now to FIG. 5, a patient path 204 is provided wherein the patient enters the main entrance 112 into the waiting room 124. After visiting reception 128, the patient proceeds to a primary care pod 130. If needed, a specialist can be 'quick' consulted at, and will come to the physician workspace using the clinic flow pattern and 3D rendered path to the desired consulting practitioner's pod entrance and workspace. Here the case can be discussed confidentially and if needed the consulted practitioner can enter the patient's exam room, providing patient-centered care. In the route as shown in 204, the patient then visits the specialist 132 in the same visit (may not be needed as specialist comes to them). The patient may then proceed to the lab 106 before exiting the building 101B.

Figure 6:
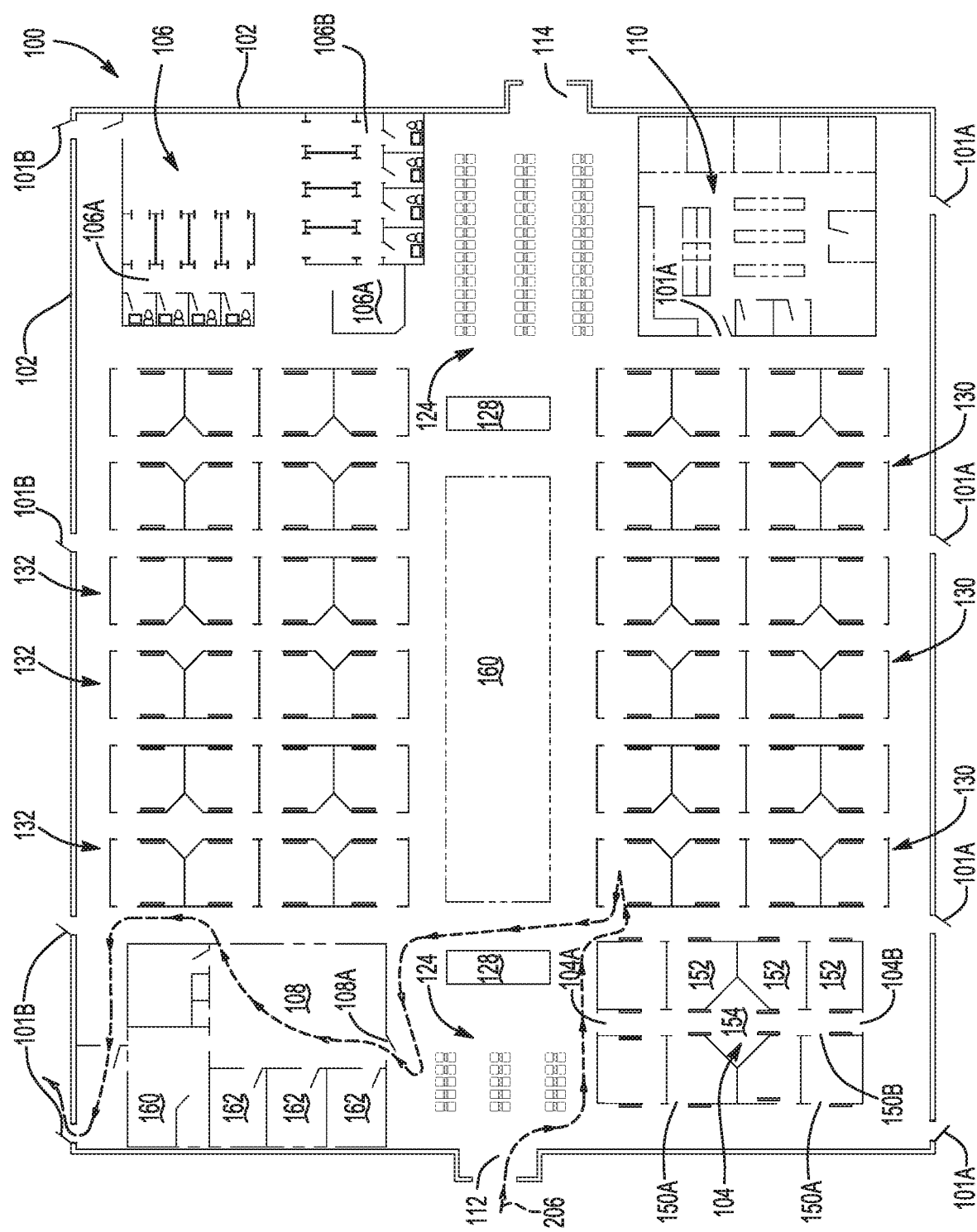
FIG. 6 depicts an exemplary building structure with illustrative flow arrows extending therethrough according to one or more embodiments shown and described herein.

FIG. 6 depicts a patient flow path 206 wherein the patient enters the clinic at the main entrance 112 and proceeds through the waiting room 124. After visiting reception 128 the patient proceeds to a primary care pod 130. The patient then visits the imaging center 108, and if needed, a specialist can be 'quick' consulted to see the patient in the imaging center, which will house additional pods, and patient exam rooms. The patient then exits the clinic at the dedicated exit 101B.

FIG. 6 further depicts a path at route 206. This route show the path of a person moving between exam rooms and through the hallway. The hallway extending between 104A and 104B is created to provide a path for physicians (and other staff) only and is intended to be a private and confidential area.

Figure 7:
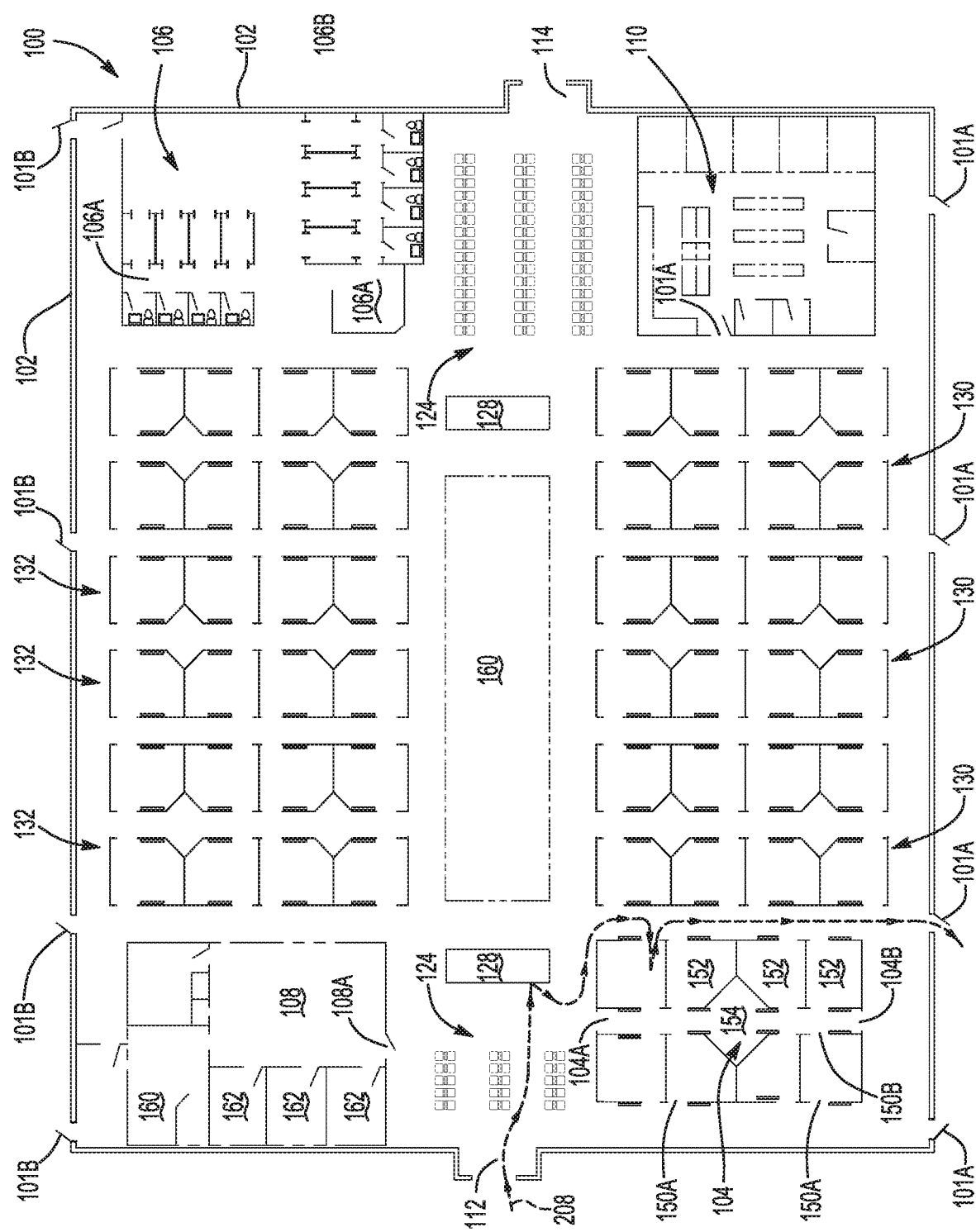
FIG. 7 depicts an exemplary building structure with illustrative flow arrows extending therethrough according to one or more embodiments shown and described herein.

Referring now to FIG. 7, a patient flow path 208 depicts wherein a patient enters the building through a main entrance 112 into the waiting room 124. After visiting reception 128, the patient may visit the urgent care 104 and exits the building through the dedicated exit 101A.

In some embodiments, a second and third floor may be provided on top of the first floor as illustrated in FIGS. 1 through 7. These additions can be added or omitted in a modular nature to suit geographical community needs. Similarly, a modular floor may be added for teaching, conference and private office use as needed. In order to provide adequate parking, while minimizing the facility's overall footprint, a parking garage will be available adjacent and connected to the main facility. The parking garage and elevators will provide multi-floor access to the main facility. The additional floors may include offices and a renal program/dialysis center accessible via the parking garage and elevators.

The clinic's lab will be available for immediate blood drawing prior to the patient's appointment. Analysis of the blood sample will take approximately 10-15 minutes and results will be electronically inputted into the clinic's EMR (electronic medical record). The results will be available to the healthcare provider that same day for assessment. This saves the patient a visit to separate medical laboratory, which is common practice, usually done one week prior to their clinic appointment.

Figure 8:
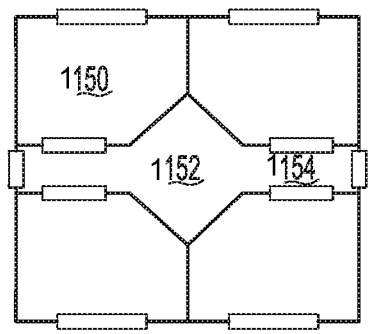
FIG. 8 depicts an exemplary exploded view of a single modular pod (comprised of 4 patient exam rooms and a dedicated work space) according to one or more embodiments shown and described herein.
Figure 9:
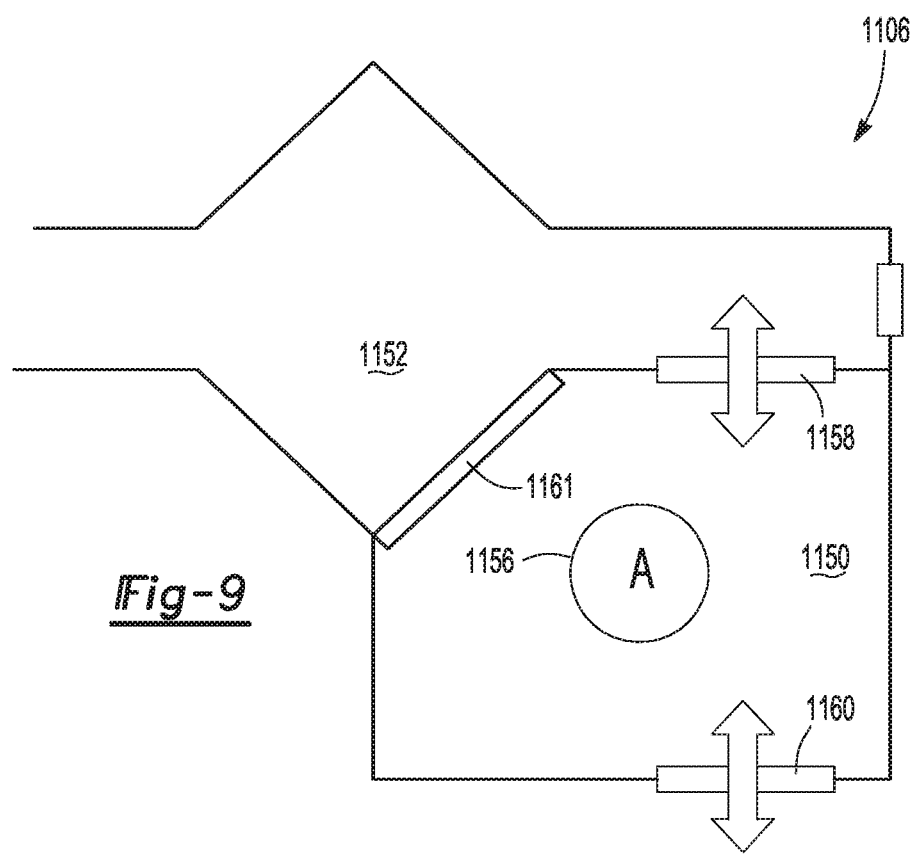
FIG. 9 depicts an exemplary exploded patient exam room and dedicated work space with access corridors designed according to one or more embodiments shown and described herein.

Now referring to FIGS. 8 and 9, each of primary care modular pods and the specialist modular pods include a centralized work area surrounded by four exam rooms, giving the provider(s) easy access to each exam room through the access hallways. Each of the exam rooms 1150 has a separate entrance/exit for the provider 1158 and a separate entrance/exit for the patient 1160. The provider also has a separate entrance/exit 1154 to the work area 1152. The plurality of entrances and exits (as shown by the plurality of doors in FIGS. 8 and 9) for the patients and physicians optimizes efficiency of the modular pods, and therefore the entire medical clinic. Each of the exam rooms in the clinic are compartmentalized, patient-centered, and facilitate a collaboration between healthcare providers and patients. Each exam room will have a unique and uniform design.

The pods are positioned adjacent to one another. Each of the pods has a hallway extending therethrough to optimize movement of healthcare providers between exam rooms, and to enable specialist physicians from the other pods to easily access the pods 1106 for 'quick' consultation.

The joint specialist pods contain at least two work spaces for physicians. The dual workspace configuration allows two specialists to work directly adjacent to one another, allowing optimization of patient care. If, for example, the patient or physician wants a second opinion, a similarly specialized physician is available to immediately provide a second opinion. This method of providing second opinions can be applied to the primary care physicians as well. All physicians, both primary care and specialist, can utilize the centralized hallways connecting the work spaces and enter through the physician entrances, to increase efficiency of movement throughout the clinic.

Each exam room will have a dedicated area for the use of audio/visual presentation 1161 (FIG. 9), which allows the patient to see their laboratory values, imaging results, and question their healthcare provider with any concerns. This design allows the patient to be more involved in their healthcare decisions, and more informed about their condition. The audio/visual presentation 1161 (FIG. 9) will display educational material while the patient waits for the physician in the exam room. The use of audio/visual technology 1161 (FIG. 9) is also integrated with the use of the novel computer program and companion mobile device application. When a healthcare provider generates a QR code using the computer program, it will be displayed on the projection area for the patient to scan using the companion mobile device application.

The patient will scan the QR code giving them access to their problem list and educational materials, such as outlined and described in the forgoing description of the computer program and companion mobile device application. The QR code may also open a link to download/view additional information critical to the patient and patient care. The exam room will contain a single swivel, reclining examination chair in the center of the room, as well as a rolling chair for the attending physician. Other components standard and necessary in typical exam rooms may also be provided.

The medical clinic may also be equipped with a paging system as a backup system, to facilitate the 'quick' consult model, however this will routinely be done through the clinic software and phone application. In each exam room audio/visual educational material will be displayed on the screen 1161 until the physician arrives. In this embodiment, the screen 161 is contained within the exam room. The screen may be any display screen, such as a monitor, projector or television, suitable to provide the relevant information to the patient.

In one aspect of the present specification, a means for enabling communication within the medical clinic regarding the occupancy of exam rooms is provided. The computer program will have a secure login for all clinic personnel (both support staff and healthcare providers). This function of the computer program can be described as a flow manager and will also facilitate the novel 'quick' consult model. This function will be available from the computer program home screen and when accessed will project to the screen. This screen will be accessible to all clinic members (both support staff and healthcare providers). By clicking the pictorial representation of an exam room, a clinic member will have the option to change the occupancy status of that exam room. The status options are: empty, filled-ready for nurse, filled-ready for doctor, filled-patient and doctor. The exam room statuses are color coordinated to make the status of the exam room visually detectable by clinic personnel. When an exam room's status is changed, the computer program will notify appropriate clinic personnel in two ways. The first notification method is a pop-up desktop notification, and the second is a mobile device notification. Combined, the flow manager, and notification systems will maximize clinic efficiency.

The next novel component of the flow manager is making the 'quick' consult model practical and functional. A healthcare provider will be able to select an exam room where they would like a colleague's consultation. Once the room is selected, a specific provider can be chosen for consultation. The provider chosen for consultation will then receive notification via the computer program in the form of a desktop notification and a mobile device notification. The practitioner providing the quick consult can navigate to the desired location using 3-D rendered paths that are consistent with the flow patterns established for the clinic.

The computer program and companion mobile device application, such as illustrated in FIGS. 10-13, are essential to accomplishing the goals of the medical clinic by increasing productivity and improving patient health outcomes. The computer program and companion mobile device application work together to enhance coordination of care, increase patient involvement in care, while also providing helpful educational material, and simultaneously integrating clinic design with novel technology such as described herein and above. The problem list, medication list, educational material, appointment information and reminders will also be instrumental in increasing patient involvement, medication adherence and patient appointment compliance. These features are available to the patient through the companion mobile device application on the patient's personal mobile device. A detailed explanation of each component is found below.

Figure 10:
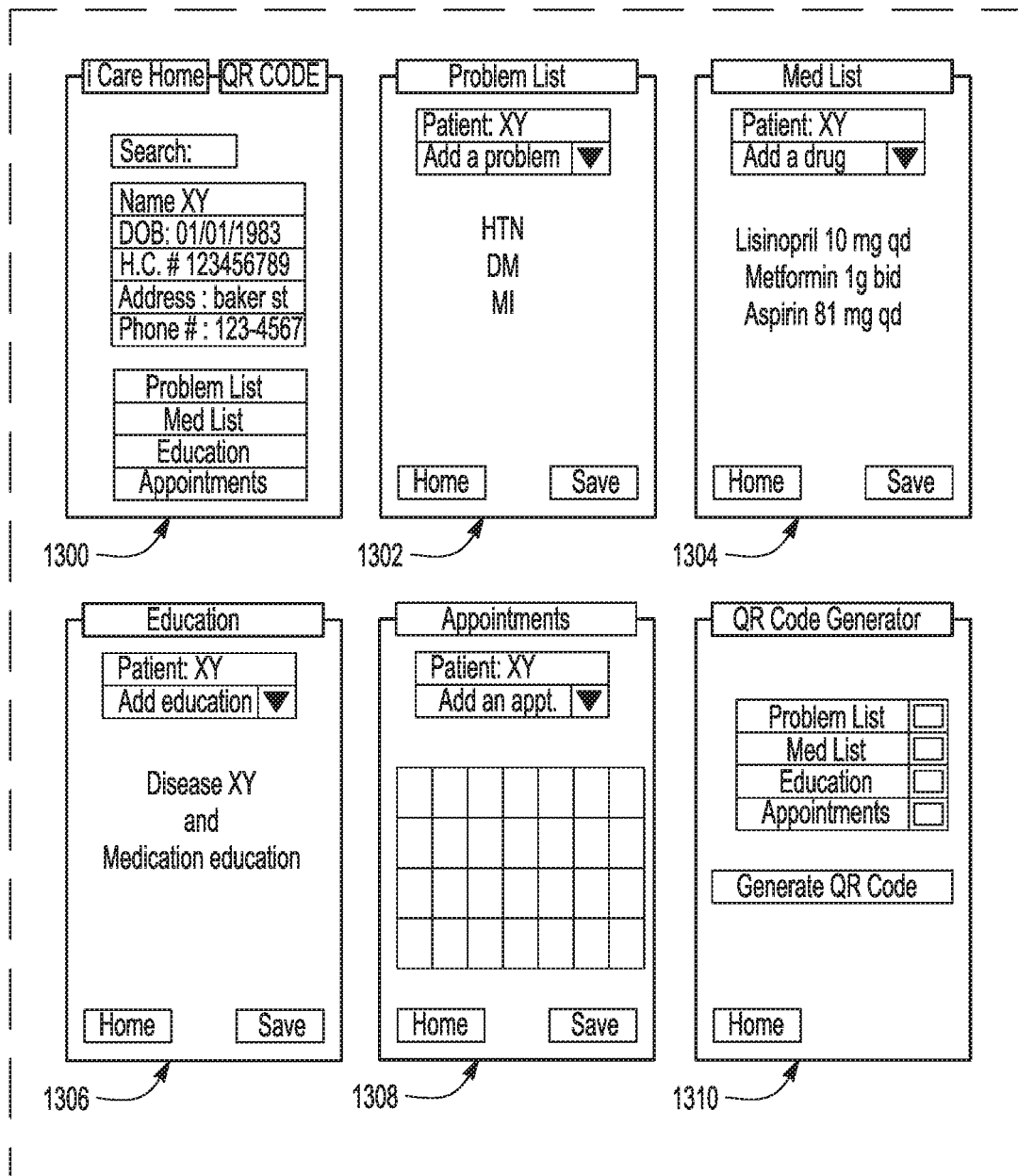
FIG. 10 depicts an exemplary screen shots of the computer program model showing information inputted by clinic personnel including patient identification information, problem list, medication list, educational material, appointments and the QR code generator according to one or more embodiments shown and described herein.
Figure 11:
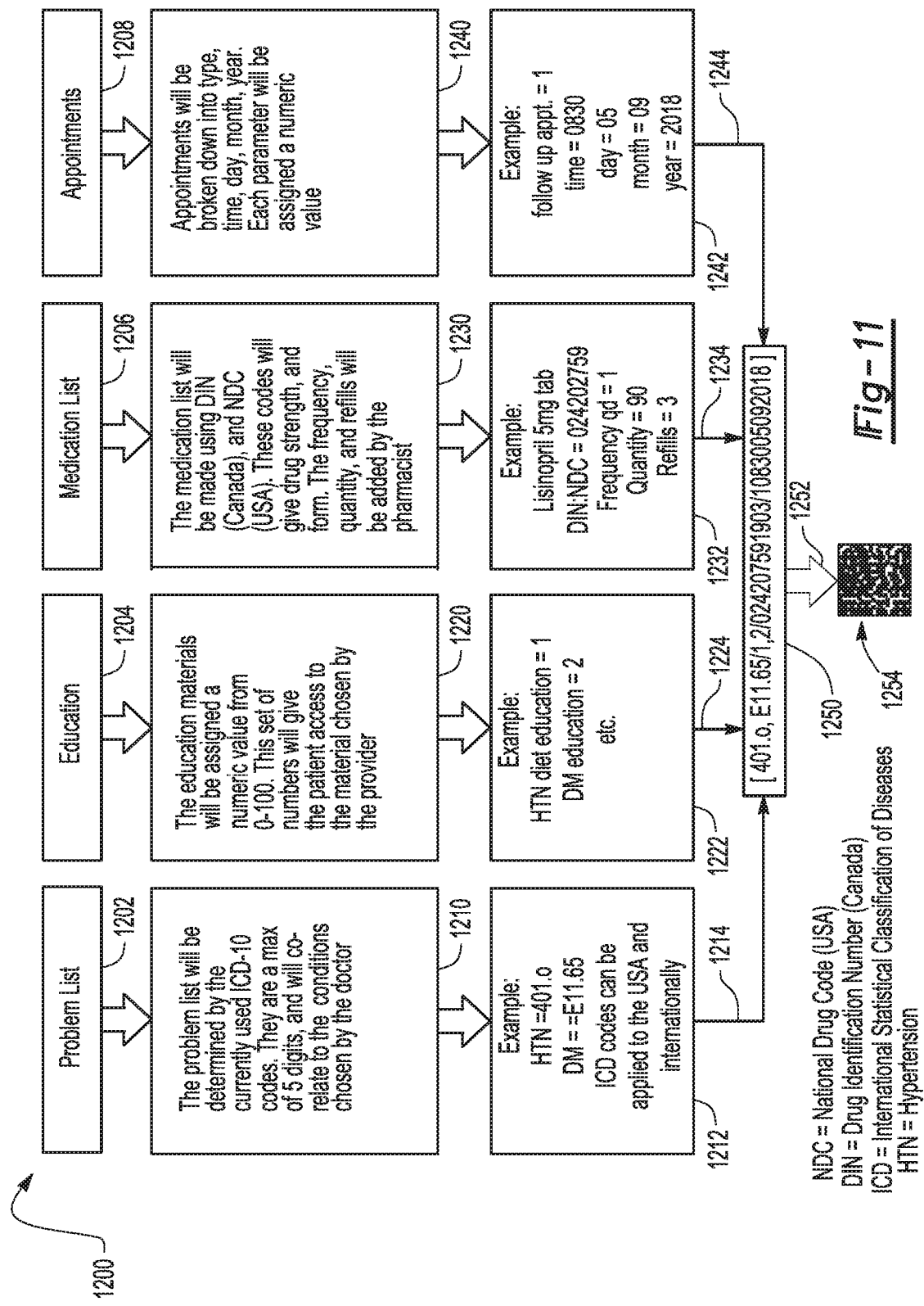
FIG. 11 depicts an exemplary flow chart of the computer program process of QR code synthesis according to one or more embodiments shown and described herein.

FIG. 10 illustrates the general interface of the computer program for healthcare providers and medical clinic personnel. FIG. 11 generally illustrates exemplary screen shots of the computer program. The first screen 1300 includes general biographical information such as the date of birth, address . . . etc. of the patient and accessible functions such as problem list, medication list, education, and appointments. This information is inputted by the physician or the medical clinic personnel. Screens 1302, 1304, 1306 and 1308 all illustrate areas for the healthcare team to input information such as the problem list, medication list, education and appointments, respectively. Screen 1310 illustrates the QR code 1254 generator.

Figure 12:
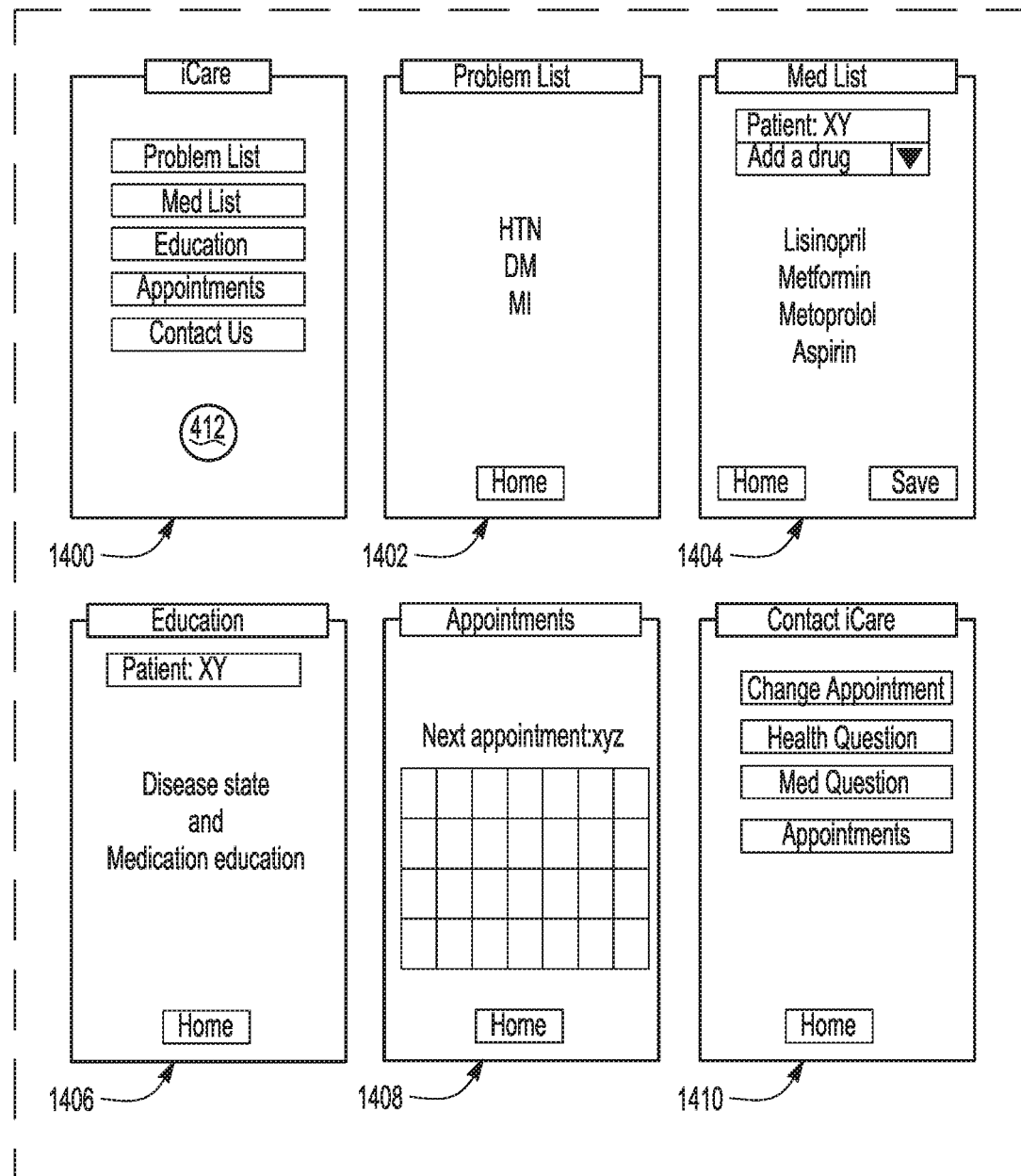
FIG. 12 depicts an exemplary screen shots of the companion mobile device application model including information accessible to the patient such as, but not limited to, problem list, medication list, educational material, and appointment information according to one or more embodiments shown and described herein.

FIG. 12 shows a general layout of the computer program, in which each clinic patient will have a profile with basic identification information (name, DOB, gender, address, phone number, health coverage identifiers . . . etc.). Within each profile, one of four functions can be accessed 1300. The functions include the problem list 1302, medication list 1304, education 1306, and appointments 1308. As described below, within each of these four categories, information can be selected/inputted by the health care team that is specifically suited to each patient. Once the information is inputted by the appropriate personnel, the information is saved to the patient's profile allowing a QR code to be generated and scanned by the patient via the companion mobile device application on the patient's personal mobile device. Once scanned the patient will have access to information and reminders that will increase patient involvement and improve health outcomes.

Figure 13:
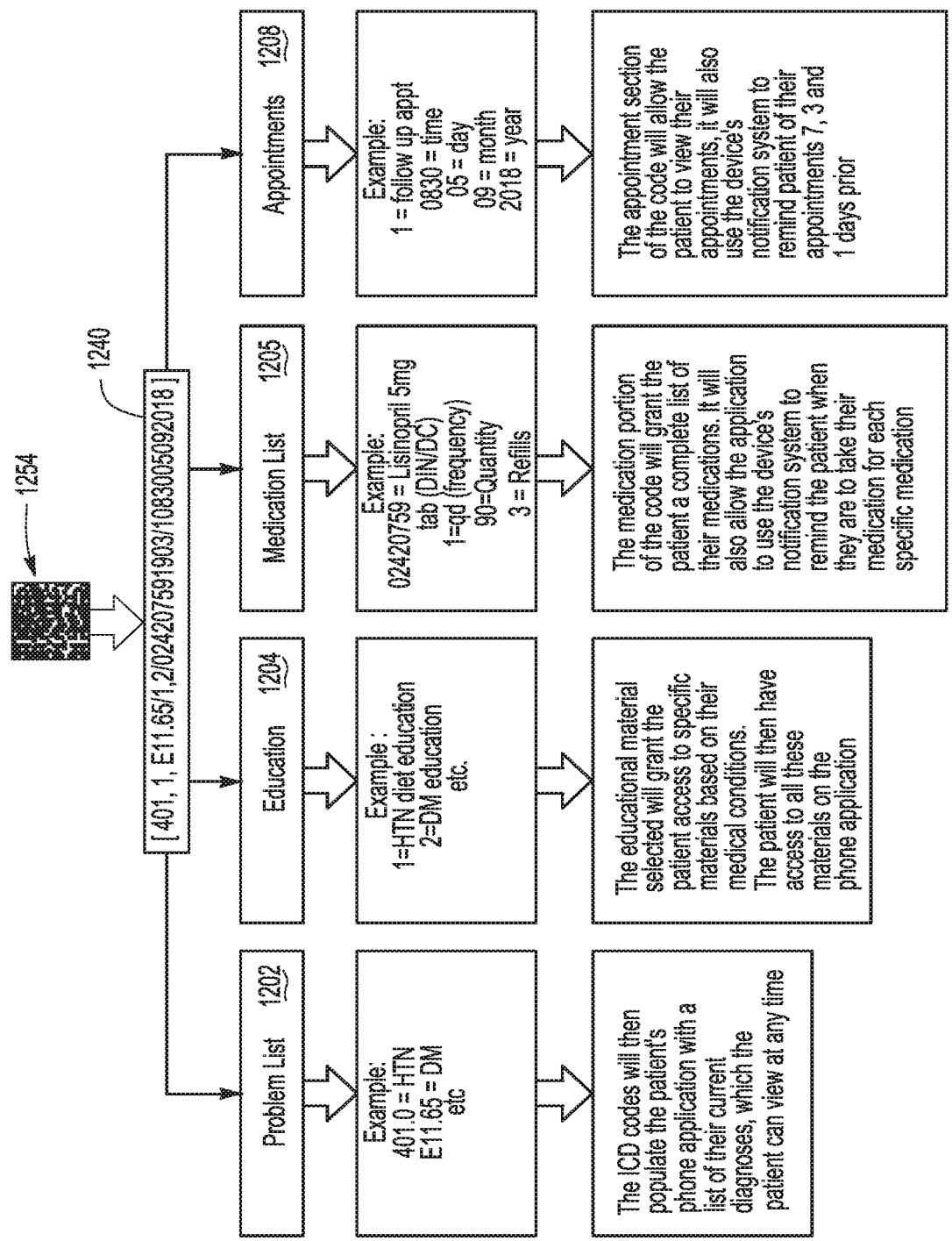
FIG. 13 depicts an exemplary flow chart of the process of decoding of a synthesized QR code by the companion mobile device according to one or more embodiments shown and described herein.

FIG. 13 illustrates a general process in accordance with the computer program QR code synthesis 1200. The problem list 1202 is inputted by the provider to grant the patient a current, inclusive problem list available to the patient on their personal mobile device via the companion mobile device application. The provider inputted problem list will computationally be translated to the appropriate, currently used ICD-10 (International Classification of Diseases) codes. This process is illustrated beginning at reference numeral 1202. An example of ICD-10 codes are provided in the flow chart of FIG. 5 at reference numeral 1212. The selected problems are inputted and converted to ICD-10 codes, then they are combined 1214 (as illustrated by the directional arrow) into the numerical code 1250. This numerical code 1250 is generated 252 into a QR code 1254, such as shown.

FIG. 12 further illustrates the education 1204 selected by the physician granting the patient access to the corresponding educational material on their personal mobile device via the companion mobile device application. The educational material is selected by the physician specifically suited to each patient. All distinct educational material will have an assigned numeric value as shown in reference numeral 1220. Reference numeral 1222 illustrates an example of these assigned numeric values. The provider selected educational material are computationally translated to their numeric value and combined 1224 (as illustrated by the directional arrow) into the numerical code 250. This numerical code 1250 is generated 252 into a QR code 1254, such as shown.

A medication list 1206 is further provided as inputted by the pharmacist, granting the patient access to their medication list and compliance reminders on their personal mobile device via the companion mobile device application. As illustrated by reference numeral 1230, the medication list is formulated using DIN (Drug Identification Number—Canada) and NDC (National Drug Code—USA). These codes give the drug, strength and form. The quantity, dosing frequency, route of administration and refills may also be added to this information. An exemplary set of codes is provided at reference numeral 1232 showing an exemplary drug, strength, form, quantity, frequency, and refills . . . etc. The pharmacist will input the medication list which will be computationally converted into a unique numeric code and combined 1234 (as illustrated by the directional arrow) into the numerical code 1250. This numerical code 1250 is generated 1252 into a QR code 1254, such as shown.

FIG. 11 further illustrates the appointments 1208 are inputted by the physician or support staff and viewable by the patient on their mobile device via the mobile application. As illustrated at reference numeral 1240, appointments are broken down into type, time, day, month and year. To generate the QR code 1254, each parameter of the appointment is computationally assigned a numeric value. An exemplary set of numeric values is illustrated at reference numeral 1242. The appointments are inputted and computationally converted into a unique code and combined 1244 (as illustrated by the directional arrow) into the numerical code 1250 This numerical code 1250 is generated 1252 into a QR code 1254, such as shown.

Collection of data as outlined above and as outlined in FIG. 10 and FIG. 11 allows the computer program to generate the QR code 1254 that is readable by the companion mobile device application. The QR codes 1254 are made available to the patient in the exam room, at reception, or in the pharmacy, electronically or in any way deemed effective and efficient.

FIG. 12 illustrates the general user interface of the companion mobile device application. Screen 1400 having the button 1412 (to enable the camera to capture the QR code). Screen 1400 also enumerates the selectable options of problem list, medication list, education, appointments or contact us. Screen 1402 illustrates the problems list, screen 404 illustrates the medication list 1404, screen 1406 illustrates the educational material available to the patient, screen 1408 depicts upcoming appointments and screen 1410 shows contact options.

The companion mobile device application utilizes the camera function 412 in virtually all mobile devices to read the QR code 1254. Upon downloading the companion mobile device application, the patient will be able to scan the QR code 1254 provided to them by clinic personnel. The companion mobile device application will open with the camera function enabled. The user can tap the circle 1412 while the camera is in view of the QR code 1254 to allow for QR code decoding. The companion mobile device application will automatically populate with the information (problem list, medication list, educational material, and appointments) attached to that unique QR code. The information previously translated into the QR code 1254 will be accessible to the patient within the companion mobile device application. The companion mobile device application will subsequently provide helpful reminders for medication adherence, medication refills, and appointments. The companion mobile device application will access the devices' notification system and remind patients of upcoming appointments 7 days, 3 days, and 1 day prior to their appointment. This allows for more efficient use of office staff time by eliminating the need to make appointment reminder calls, while enhancing appointment attendance. The application will also provide medication adherence reminders. The reminders will be specific to the drugs and medication schedule that the patient is prescribed. This will improve adherence to therapies known to improve patient health outcomes. Furthermore, the companion mobile device application will have a function allowing the patient to contact the clinic via email 410. This function will be stratified, allowing the patient to select the general purpose of their inquiry. Each selection will open a template email and allow the patient to send their comment/question/concern to a generalized email account(s) and include their phone number for correspondence. Emails will be sorted by importance and urgency, and promptly responded to accordingly. The companion mobile device application will eventually be developed to allow the patient to track their home health information, such as blood pressure, blood sugar readings, etc. and pertinent clinical laboratory parameters.

Figure 14:
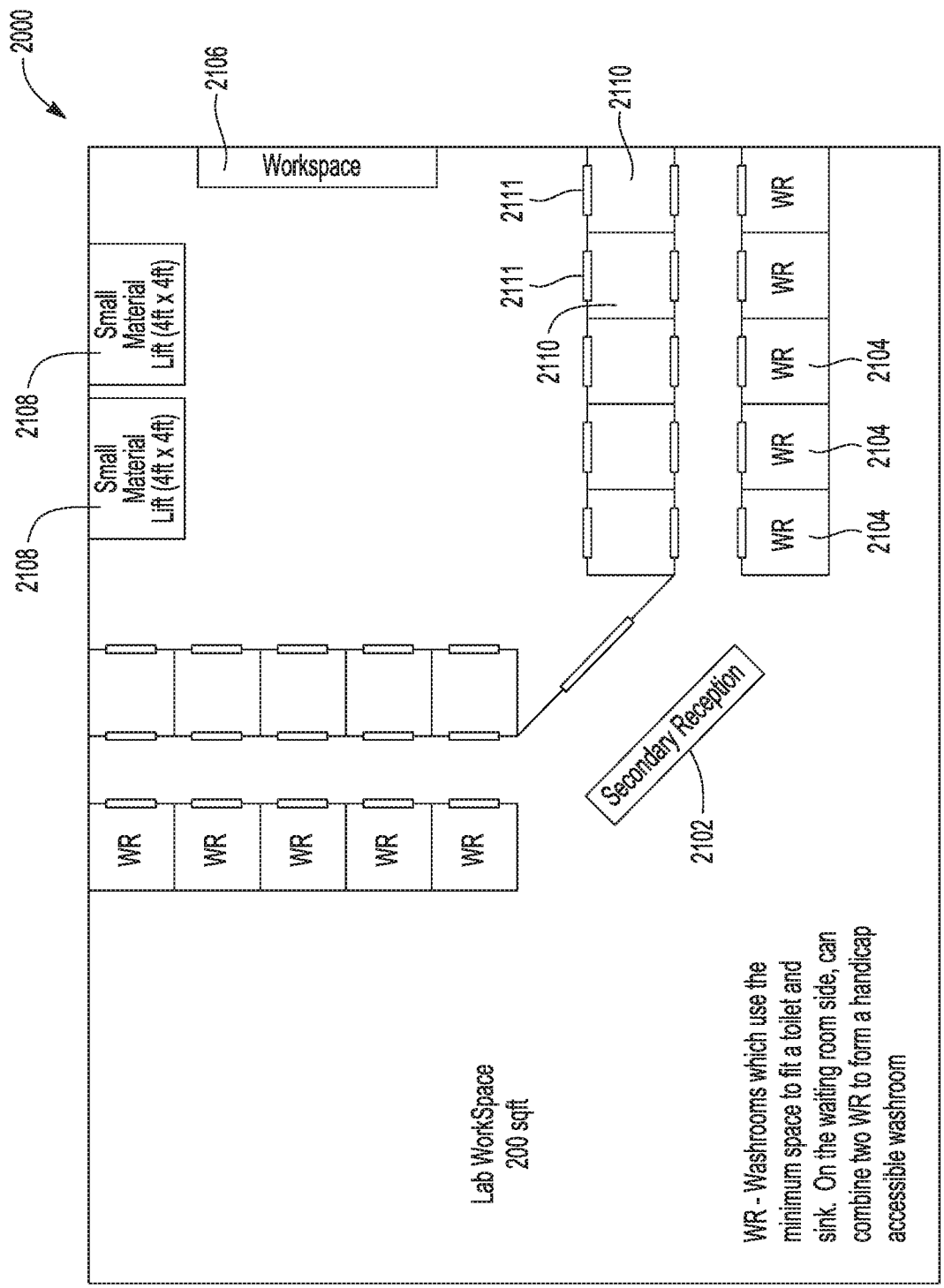
FIG. 14 depicts a layout of a lab according to one or more embodiments shown and described herein.
Figure 15:
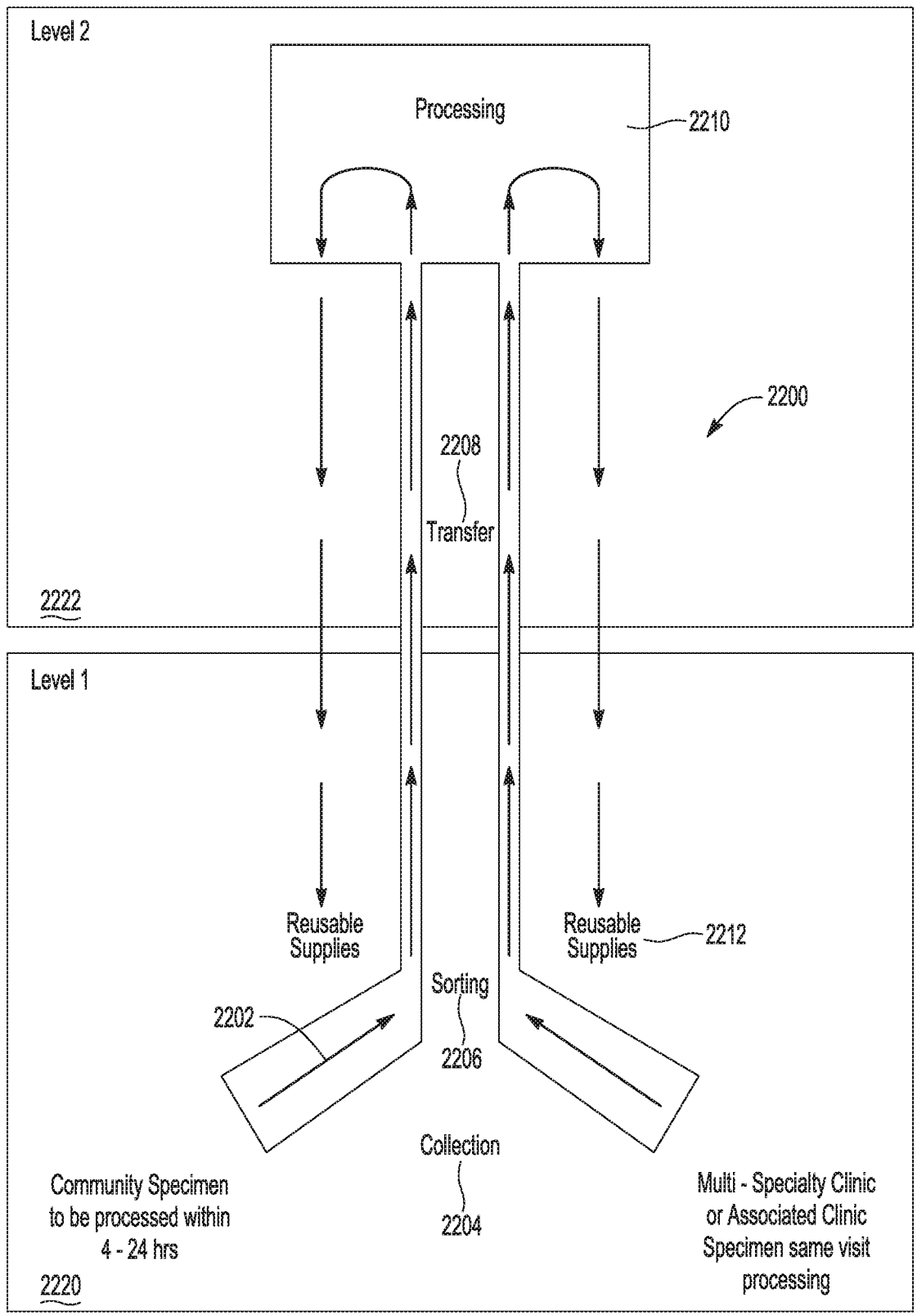
FIG. 15 depicts a multi-level physical layout of a building wherein level 1 includes collection and sorting and level 2 includes transfer and processing according to one or more embodiments shown and described herein.

Now referring to both FIGS. 14 and 15, the present system solution initially includes a physical arrangement 2000 of the bloodletting stations and sorting of specimens including a first level 2220 and a second level 2222. This is on the first floor of the clinic immediately below the larger full laboratory (level 2) where specimens are processed. On level 1 (2220), such as shown in FIG. 14, each phlebotomist has their own room 2110 for bloodletting and immediate transfer of specimen to the sorting area. A plurality of washrooms 2104 are used for urine collection specimens are immediately across from the bloodletting rooms 2110 used for that particular patient. The phlebotomist on collecting the desired specimens transfers them to the sorting area directly without having to leave their room through the window 2111 identified in FIG. 14. As further illustrated in FIG. 14, the layout includes a secondary receptionist 2102 to greets patients and to direct patients to the proper areas. The work space in the layout 2000 further includes a workspace 2106 and at least one lift or other elevators 2108 configured to move material to Level 2.

FIG. 15 illustrates a unidirectional flow 2202 (as evidenced by the arrow 2202) of the specimen from the time of bloodletting etc. to sorting to transfer up a lift system directly upwards to the full laboratory on the floor immediately above the specimen collection site. The specimen moves from Level 1 2220 from collection 2204, to sorting 2206 up though the transfer 2208 as illustrated by the unidirectional arrow 2202. The specimen then moves up to level 2 2222 up to processing 2210. On level 2 2222 of the full laboratory, the specimen is processed within 10 minutes for patients who are attending clinic on the same day so the results are immediately available for their assessments. The reusable supplies are then transferred back down to level 1 2220 where any reusable supplies 2212 are transferred back. The transfer occurs on a lift or other similar transportation system configured to transport the physical specimens.

This physical set up and procedure for laboratory specimens collection and processing has the potential to reduce emergency room utilization as when labs are done 1-2 weeks prior to the clinic visit, patients are often directed to the emergency room to deal with issues on their laboratory investigations because clinical assessment is not immediate at the time of the testing. In this model, because the testing is the same day as the clinic visit, patients will be assessed and issues dealt with identified on their lab work on the same day.

This also enables clinicians to react to real-time immediate results in their clinical assessments. It reduces the need for repeat lab work due to data that is not most current. The present 2 level (or otherwise multi-level) system is advantageous because if the lab was next to the clinic on the same floor, it would not be as efficient a process with collection, processing and transfer back and forth of specimens and supplies. The 2 level arrangement allows samples to be transferred up to maximize floor space to mitigate the need of transfer carts, people . . . etc. to physically move the samples across a building. Moving specimens vertically and mechanically is significantly more efficient.

It allows for increased utilization of more cost effective real-time immediate community-based clinical assessments and less reliance on emergency room departments and hospitals to be able to do real time immediate laboratory investigations and assessments.

It is noted that the terms "substantially" and "about" may be utilized herein to represent the inherent degree of uncertainty that may be attributed to any quantitative comparison, value, measurement, or other representation.

These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination.

It is therefore intended that the appended claims cover all such changes and modifications that are within the scope of the claimed subject matter.

We claim:

1. A medical facility comprising:
a building, the building including a plurality of four segregated specialty areas, each of the specialty areas positioned in the outer four corners of the building;
the specialty areas bring a laboratory, an urgent care facility, a pharmacy, and an imaging center;
the laboratory having a first level and a second level, the first level configured to collect samples from patients to be tested, the second floor configured to process the samples collected on the first level; and
a transportation system connecting the first level to the second level, the transportation system configured to transport samples collected on the first level to the second level for immediate processing of the samples on the second level thereby enabling expediting processing of the samples collected on the first level of the laboratory of the medical facility, the transportation system being a lift configured to move samples between the first level and the second level, the second level being directly above the first level;
the first level being a specimen collection site; and
the second level being a specimen processing site.

2. The medical facility of claim 1 wherein the transportation system transports reusable supplies back down to the first level after processing.

3. The medical facility of claim 1 wherein a plurality of lifts are provided in the laboratory enabling communication between the first level and the second level.

4. The medical facility of claim 1 wherein the transportation system is a elevator configured to hold only samples and supplies.

5. A method of using the lift of the medical facility of claim 1 comprising the steps of:
collecting a specimen on the first level;
sorting said specimen;
transferring said specimen directly upwards to the second level immediately above the first level;
processing said specimen on the second level, processing said specimen within 10 minutes;
transferring reusable supplies from the second level back down to the first level; and delivering real-time immediate laboratory investigations and assessments from said specimen to a clinician.

* * * * *